United States Patent [19]

Brinton et al.

[11] Patent Number: 4,696,896

[45] Date of Patent: * Sep. 29, 1987

[54] **GONOCOCCAL PILI PROCESSES FOR THE PREPARATION THEREOF AND THE USE THEREOF FOR THE DETECTION OF AND PREVENTION OF INFECTIONS CAUSED BY *NEISSERIA GONORRHOEAE***

[75] Inventors: Charles C. Brinton, Pittsburgh; John C. McMichael, Imperial, both of Pa.

[73] Assignee: Bactex, Inc., Pittsburgh, Pa.

[*] Notice: The portion of the term of this patent subsequent to Jul. 24, 2001 has been disclaimed.

[21] Appl. No.: 590,544

[22] Filed: Mar. 19, 1984

Related U.S. Application Data

[63] Continuation of Ser. No. 427,126, Sep. 29, 1982, abandoned, which is a continuation of Ser. No. 188,463, Sep. 18, 1980, abandoned, which is a continuation of Ser. No. 571,200, Apr. 25, 1975, abandoned.

[51] Int. Cl.[4] .................. G01N 33/531; G01N 33/544; G01N 33/569; A61K 39/095
[52] U.S. Cl. .......................................... 435/7; 424/92; 435/820; 435/871; 436/528; 530/352; 530/825
[58] Field of Search .................. 435/7, 30, 34, 170, 435/272, 871, 820; 260/112 R; 424/92, 87; 436/511, 528; 530/825, 352

[56] References Cited

U.S. PATENT DOCUMENTS 4,461,838  7/1924  Brinton et al. ..................... 436/511

OTHER PUBLICATIONS

J. B. G. Kwapinski *Methodology of Immunochemical and Immunological Research*, Wiley-Interscience, New York, 1972, pp. 296-304.
Buchanan et al., J. Clin Invest 52 (1973) 2896-2909.

*Primary Examiner*—Esther M. Kepplinger
*Assistant Examiner*—David A. Saunders
*Attorney, Agent, or Firm*—Omri M. Behr

[57] ABSTRACT

There are provided a crystalline and single rod products derivable from the Pili of Type 1 and Type 2 *Neisseria gonorrhoese* organisms. There are provided methods of growing said organisms to produce the maximum yield of Pili and procedures for purifying said Pili to produce said crystalline material. There are further provided methods of utilizing said Pili to determine the presence, in a system infectable by *N. gonorrhoese* organisms, of antibodies to the Pili of said organisms, and methods of serotyping said Pili. There is also provided a mode of utilizing said crystalline material to provide a substantial degree of immunization infection by *N. gonorrhoese* in mammalian systems susceptible to such infection.

19 Claims, No Drawings

GONOCOCCAL PILI PROCESSES FOR THE PREPARATION THEREOF AND THE USE THEREOF FOR THE DETECTION OF AND PREVENTION OF INFECTIONS CAUSED BY NEISSERIA GONORRHOEAE

This application is a continuation of application Ser. No. 427,126, filed 9/29/82 which in turn is a continuation of Ser. No. 188,463, filed 9/18/80 which in turn is a continuation of Ser. No. 571,200, filed 4/25/75(now all abandoned).

DESCRIPTION OF THE PRIOR ART

The infection caused by the organism *Neisseria gonorrhoeae* commonly known as Gonorrhea is a venereal disease of an extremely wide spread nature in humans. The disease usually manifests itself by a visible discharge in males but frequently is undetected and undetectable by external symptoms in females infected therewith. Heretofore, the only reliable mode of detection of infection has been by culturing discharges or mucus fluids believed to contain the organism. Such cultures take a period of more than one day to grow. Because of the social opprobrium attached to the disease and the reluctance of many persons infected therewith to return to the test clinic, it has long been desirable to provide a screening method which can give a reliable indication of possible infection or noninfection during a time for which it is reasonable to require the test subject to remain in the clinic.

Furthermore, heretofore there has been no development of any method of immunization against infection with the organism of *N. gonorrhoeae* in humans. One of the greatest problems associated with research in this area has been the fact that the organism only appears to infect humans and chimpanzees and, while there is a reasonable degree of correlation between results in chimpanzees and results in humans, such a correlation is not absolute. Chimpanzees, although reasonably satisfactory as research models, are extremely expensive as research subjects.

Four distinct colonial variants of *Neisseria gonorrhoeae* have been characterized. These four variants fall into two distinct categories. Variants $T_1$ and $T_2$ produce experimental infection in human volunteers whereas Type $T_3$ and $T_4$ are not known to cause infection. The first group may be distinguished from the second group in the observation that the first group possess filamentous structures on the surface of the colonial variants whereas the second group are devoid of these filamentous structures. These filaments are designated as Gonococcal pili (hereinafter G. C. pili). In 1973 two papers were published purporting to show the isolation of $T_1$ and $T_2$ pili from *N. gonorrhoeae* and further purporting show the formation of antibody response thereto (Buchanan, et al., J. Clin. Invest. 52, 2896-2909 (1973) and Punsalang and Sawyer, Infect. Immun. 8, 255-263 (1973). See also Buchanan, et al., J. Clin. Invest. 51 17A (1972). The basic method utilized by Buchanan is acknowledged as Reference 41 in the 1973 paper as having been developed by Charles C. Brinton, one of the inventors herein (C. C. Brinton, Trans. N.Y. Acad. of Sci. 27, 1003 (1965)), as well as by Punsalang and Sawyer.

SUMMARY OF THE INVENTION

The invention relates to the provision of purified pili of type $T_1$ and $T_2$ *Neisseria gonorrhoeae* organisms as well as the $T_R$ subvariants thereof if desired, in crystalline form (hereinafter GC pilus crystals).

GC pili are isolated from either surface culture or deep liquid culture of the corresponding organism. The method of surface and deep culture of *N. gonorrhoeae* cells are substantially conventional. In a modification of the deep culture method, a high surface area, rection inert, medium, is added to the culture to aid in the purification. A diatomaceous earth such as Celite has been found suitable.

In the case of the surface growth, the entire growth, that is to say, the cells and pili are removed from the culture medium and suspended in an aqueous medium at a predetermined pH below 9.2. Where it is desired to isolate $T_2$ pili only any pH above pH 5.5 and below pH 9.2 is suitable. Where it is desired to isolate $T_1$ pili either per se or in the presence of $T_2$ pili, a pH below pH 7.7 suitably around pH 7.0 is required. In the case of deep culture growth, such as suspending step is not necessary.

It has also been found that pilus crystals are soluble below 4.5 and are substantially reconstitutable when the pH is again raised above this volume provided it had not been reduced below about pH 2.5.

The portions of said suspensions which are soluble are then separated from the portions of the suspension which are insoluble. While filtration may be utilized for this separation it is generally preferred to utilize centrifugation. The supernate of the centrifugation (and the filtrate in the case of filtration) is discarded and the residues retained. In the next step of the purification procedure, the constituent portions of the Gonococcal pili are brought into solution and separated from the remaining material. In the case of the surface culture this material will include whole cells and debris and in the case of the deep culture, will additionally include the high surface area material such as the Celite.

The solution of the Gonococcal pilus crystals may be achieved by two (2) different but closely related methods. The solution of the material of the gonococcal pilus crystals depends upon the breaking of inter pilus rod non-covalent bonds involving the peptide material which constitutes a major portion of the pili, while leaving the covalent bonds intact. That is to say, the use of a solubilizing agent which will not denature the peptide, but merely disaggregate the crystals into single pilus rods. Such agents may be independent of pH such as aqueous urea, sufficient water to lower the ionic concentration of an aqueous suspending medium below 0.002M, sufficient salt, suitably salts of alkali or alkaline earth metals and the anions of mineral acids to raise the ionic strength above 4.4M, urea to a concentration of between about 3M and about 5M and sufficient sucrose to raise the concentration above about 50% weight per volume. The pilus crystals are reprecipitated by raising the ionic strength above about 0.05M by the addition of salts of mineral acid anions and alkali and alkaline earth metals; the addition of sufficient water to reduce the salt concentration below an ionic strength of 0.5M sufficient buffer suitably tris buffered saline to provide a medium of ionic strength about 0.05 about 0.5M at a pH of about 4.5 to about 9.2, and sufficient water to reduce the sucrose concentration below 40% by weight respectively. The agents may also be pH dependent such as basic buffers such as a tris buffer which will raise the pH to a level of from about pH 9.3 to about pH 11 for $T_2$ pili or from about pH 7 to about pH 8.6 for $T_1$ pili. Said range being determined by the commencement of solubility at the lower end and the commencement of danger of denaturation at the upper end. It has been observed however that even where the pilus structure is denatured by these or other methods to the extent that the pili will not recrystallize, their antigenic characteristics are apparently substantially unaffected.

After addition of the solvating medium to the solid residues mentioned above, the soluble and insoluble portion of said second suspension are again separated. As before, this separation may be by filtration or centrifugation, suitably centrifugation.

The centrifugation method may be either simple or modified. In the simple centrifugation method, the suspension is run in a low speed centrifuge, the supernatant retained and the residue set aside. Where it is desired to raise the yield, the residue is re-suspended, re-centrifuged, the residue discarded, and the supernatant combined with the immediately previous supernatant. The combined supernates are then subjected to high speed centrifugation to remove the last traces of small debris in the residue and the supernate then set aside for use in the succeeding precipitation step.

In the modified form of the centrifugation process, the solubilized pili, that is to say, either those suspensions at elevated pH or those in an aqueous noncovalent bond breaking medium, such as urea, are mixed with aqueous caesium chloride. Since the caesium chloride gradient method involves centrifugation, complete separation of the debris is not necessary, however, a cleaner result is obtained by the use of either prefiltration or precentrifugation. The mixture in caesium chloride is then subjected to centrifugation in the conventional manner for caesium chloride separations and the absorption at various density gradient levels measured. The location of the major peak, suitably measured at 280 nm indicates the location of the pilus solution.

Utilizing either of the methods of centrifugation, the aqueous fractions containing the pilus solutions are then treated in a manner conducive to the precipitation of the pilus crystals. This may be done by the lowering of the pH where the pH has been raised, or by removal of the noncovalent bond breaking agent, the caesium chloride or, alternatively the addition of a precipitating agent such as ammonium sulfate. Precipitating conditions may be achieved either by dialysis or by direct addition.

Upon lowering of the pH and removal of the bond breaking agent, GC pilus crystals will form. The GC pilus crystals are then removed from the aqueous medium either by filtration, or, more suitably low speed centrifugation. The supernatant is separated and the thus obtained GC pilus crystals are dried under reduced pressure, if desired, or stored in a suitable aqueous medium. While it is desirable to keep the crystals at reduced temperatures in a sterile medium, this does not appear to be essential for their stability in the absence of bacterial contamination.

It should be noted that the pilus crystals are in fact agglomerations of single pilus rods having a high molecular weight. Thus, where the medium containing the solubilized pili has been purified by high speed centrifugation with, if desired, sterilization, thru a millipore (suitably circa 0.45 micron) filter, the individual pilus rods may be precipitated by ultra high speed centrifugation suitably above 60 KG.

It has also been found that where pili of the very highest purity are not required, a convenient and rapid abbreviated purification process is quite satisfactory. In this procedure the entire gonnococcal growth is transferred into a high pH buffer, suitably an ethanolamine buffer at a pH above the solution point of the variant ($T_1$ or $T_2$) in question preferably about pH 10.0 to ensure total solution, the solids removed by filtration or centrifugation and the pH dropped-suitably but not essentially by dialysis.

Indeed pH control to, say, pH 8.6 in the first instance will crystallize out $T_2$ pilus crystals and a further drop to below pH 7.7, say to pH 7 will crystallize out $T_1$ pilus crystals. Thus indicating in one step the nature of the variant growth in question. This latter is merely confirmatory since a competent bacteriologist can differentiate between the two forms by inspection of their colonies.

Alternatively, pilus crystals may be precipitated by the addition of ammonium sulfate. An anionic concentration of between about 4% and 7% of saturation (at room temperature) will precipitate $T_2$ pili as crystals, while $T_1$ pili are precipitated by between 5% and 10% of saturation.

The GC pili have been subjected to SDS polyacrylamide gel electrophoresis and show a major and a minor band. The major band, designated GC pilin shows it to comprise phosphoglycoprotein material.

The $T_2$ GC pilin has further been shown to comprise a peptide portion of $200 \pm 9$ amino acids, between 2 and 3 phosphate groups, and between 1 and 2 hexose sugars, and is substantially soluble in aqueous media at a pH greater than 10.1 and substantially insoluble in aqueous media at a pH of less than 8.6 both pH's being measured at 20° C.

The major portion of $T_2$ GC pili, namely $T_2$ GC pilin has a molecular weight, as determined by SDS acrylamide gel electrophoresis of $21,500 \pm 1000$ daltons.

The GC pili isolated from type $T_1$ *N. gonorrhoeae* growth appear to be extremely similar immunologically to those isolated from type $T_2$ *N. gonorrhoeae*.

By comparison Type $T_1$ GC pili are substantially soluble in aqueous media above about pH 8.5 and substantially insoluble in aqueous media at a pH of less than 7.7, both pH's being measured at 20° C. Type $T_1$ GC pilin has a molecular weight of $22,000 \pm 1000$ as determined by SDS acrylamide gel electrophoresis.

GC pili have been isolated from cultures of more than 20 different strains of *N. gonorrhoeae*. When injected into test animals GC pilus crystals as well as single rod pili and the eluate from SDS acrylamide gel electrophoresis will cause the formation of antibodies in the serum of the test animals.

When GC pilus crystals are treated, either per se or in a suitable suspending medium, with serum containing anti-bodies thereto, the crystals will agglutinate. This agglutination is readily observable most suitably in a dark field microscope but also by other means, and provides a simple and immediate test for the presence of the pilus antibodies in a test serum.

Among the uses of the test may be mentioned screening for gonnorhea to select individuals for culture testing, identification of high risk individuals distinguishing new, from old infections in a particular individual, indentifying the strain responsible for a local epidemic and strains responsible for particular symptoms.

It should be noted that while this test is useful for the determination of the presence of antibodies to GC pili in a test sample, it is not possible to determine directly whether the subject from whom the serum was drawn has active gonorrhoeae or has been infected in the past and is merely a carrier of antibodies. It should be further noted that a very recently infected (i.e. in the previous 2 or 3 days) subject may not give a positive response since there may not have been sufficient time for the body to create a sufficient concentration of antibodies to give a detectable titre.

It has been noted that the pili of *N. gonorrhoeae* organisms contain one or more immunological determinants selected from a group of at least four such determinants. Thus, the antibody agglutination reaction will occur between pili and a serum containing antibodies against at least one of such immunological determinants. The strength of the response will depend upon the concentration of antibodies in the test serum sample and equally the number of interacting immunological determinants on the pili and in the serum.

It is thus possible, given say, four different GC pilus samples known to contain at least one of the aforesaid determinants to rapidly test for the presence of the corresponding antibodies to GC pili in any test serum.

Similarly, where a source of organisms is available and may be readily cultured the pili from said organisms are isolatable. Since standardized sera containing antibodies against any predetermined one of the four antigenic determinants of GC pili are available as a result of the present invention, said pili from the unknown test source are serotypable as to the identity and number of these determinants thereon. This procedure will greatly assist the epidemiological work connected with infection tracking of Gonorrhea.

Pili may be absorbed on various carriers known to immunological testing such as latex, washed red blood cells, charcoal, polyacrylamide, agarose, and the like to provide the substrates for serum or plasma agglutination tests.

The availability of pili also provides the basis for haemagglutination and haemagglutination inhibition tests. Both tests depend upon the principle that pili contain specific combining sites which will interact with red blood cells. Thus, where pili and blood cells are incubated together the red blood cells will give a diffuse agglutinated pellet by gravity settling. If no pili are present in the test medium the red blood cells settle to give a clearly defined pellet by gravity settling. This provides a means of testing for the presence of pili in a solution.

In the haemagglutination inhibition test, a test serum believed to contain antibodies to GC pili is added to a solution containing a predetermined quantity of pili and the mixture incubated and centrifuged. Pili interacting with antibodies thereto will be precipitated. The supernate is then added to red blood cells. When all the pili have been reacted with the antibodies in the test material, a sharp pellet (i.e. no agglutination) will result. It will be understood by those skilled in the art that such a test has significance when run against controls (i.e. no antibodies) and at predetermined dilutions.

The accuracy of this test is raised if the serum is first treated with washed red blood cells (i.e. prior to addition to pili). This procedure removes factors in the serum which would cause agglutination of the red blood cells regardless of the presence of pili.

Heretofore no mode of immunization against *N. gonorrhoeae* in humans has in any way been possible. It has been found that when human volunteer subjects were injected with a sufficient quantity of GC pilus crystals, suitably of the order of from about 2 to about 100 micrograms per kilogram of body weight of said pili to raise the antibody level of their serum to a PAT (Pilus Agglutination Test) titer of at least 100, a degree of protection of at least 1.6 log cycles was obtained. That is to say, that the subject was able to resist infection by a counted number of organisms of the strain from which the injected GC pilus crystals were derived, of approximately 1.6 orders of magnitude greater than that required to bring about infection in control subjects in the un-immunized state. No toxic effects attributable to the pili have been observed from the injection of GC pilus crystals. Human subjects having a titer of up to 200 appear to be unaffected and the test primates (Rhesus monkeys) have been subjected to titer levels of about 10,000 in the PAT Test without any ill effects whatsoever being noted. It has further been noted that it appears to be advisable that the injections of GC pilus crystals, in a suitable carrier medium, be made over a somewhat extended period suitably a period of up to about 5 weeks. Administration may be in between 1 to 5 aliquots of GC pilus crystals, single rod pili, or any suitable source of G.C. pilin. A spreadout rate of administration while helpful is not essential. This rate of administration permits the gradual build-up of antibodies in the system.

It should further be noted that no local adverse reaction against the crystals at the point of injection has been noted in injections in a subject to whom the crystals had already been administered at a previous point in time.

In view of the existence of several antibody determinants as mentioned hereinabove, it is desirable to administer pilus crystals, single rod pili or other sources of G.C. pilin containing each of the known determinants in order to obtain maximum protection.

DESCRIPTION OF THE PREFERRED EMBODIMENTS

Preparation of GC Pilus Crystals

Growth of *N. gonorrhoeae* Organisms Surface Culture

*Neisseria gonorrhoeae* is found in four (4) colonial forms arbitrarily designated types $T_1$, $T_2$, $T_3$ and $T_4$. This designation however is generally accepted. Type $T_1$ and $T_2$ organisms are the causative organisms of the disease Gonorrhea in humans and only these forms possess pili. The procedures set forth below are applicable to the growth of type $T_1$ and type $T_2$ organisms. It should be noted that strains of *N. gonorrhoeae* are isolatable from body secretions taken from human patients. Such secretions will usually contain not only the desired $T_1$ or $T_2$ types but also the unpiliated $T_3$ and $T_4$ types. Further, it should be noted that a culture which commences as, say, a fairly pure $T_2$ type will in due course, upon subculture, produce nonpiliated $T_3$ and $T_4$ types as well as $T_1$ types.

In the culture of $T_1$ and $T_2$ colonial variants a third piliated variant, arbitrarily designated $T_R$ is noted. This third colonial variant has a rough appearance, and while is completely characterized is believed to be closely related to the $T_1$ and $T_2$ types as these types are yielded upon subculture of $T_R$ colonies. The yield of pili from $T_R$ types is the same as from $T_2$ cultures.

In order to maximize production of either $T_2$ or $T_1$ pili, certain preliminary procedures should be followed.

The original samples are cultured on Thayer Martin (T-M) plates which allow the growth of *N. gonorrhoeae* inhibiting the growth of most other bacteria. Since T-M plates are not suitable for distinguishing colonial types, colonies from the T-M plates are streaked onto a suitable growth medium (GC medium, Catalog No. 0289-1 Difco) for example). A succession of subcultures are then prepared from single colonies on the medium (hereinafter GC medium) until the colonies comprise greater than about 90% of the desired type. While the procedure may be employed equally well for type $T_1$ as for type $T_2$, and, as has been shown, type $T_1$ and type $T_2$ are immunologically similar, it is preferred to maintain separation of the types. Hereinbelow $T_2$ will be discussed. Except where the differences are specifically noted, growth procedures for $T_2$ are equally applicable to $T_1$. When the growth on a plate shows greater than 90% of, say, $T_2$ colonies, the growth is removed from the plate and suspended in a suitable freezing medium, for example, BSA-glutamine, divided into aliquots, and stored at reduced temperatures, suitably of the order of $-70°$ C. to $-196°$ C.

It should be noted that, as stated heretofore, samples with an initially high proportion of $T_2$ have a tendency, upon subcultures, to become unstable and yield lower amounts of $T_2$. Hence, in growing the cultures, care must be taken on the one hand to ensure a high initial proportion of $T_2$ organisms and on the other hand, care must be taken to utilize a sufficiently "young" strain, that is to say, one that has not been overly often subcultured, to guard against the occurrence of instability. When it is desired to produce $T_1$ pili, it is even more important than in the $T_2$ case to use an inoculum containing over 90% $T_1$.

The inoculum for pilus production is prepared by streaking the primary, suitably but not necessarily, frozen, aliquots on a GC medium petri dish and incubating for between 12 and 24 hours. Twelve to 15 hours for strains with more unstable $T_2$ types and 12 to 24 hours for strains with more stable $T_2$ types. It is preferred to grow the inoculum at a temperature of between 35° thru 37° C., although 35° C. is deemed preferable. High humidity conditions are also deemed desirable. At humidities of less than 70% the pilus yield has been noted to be lower than at higher humidities. It is therefore deemed desirable to operate at a humidity of between 70% and 90%. While the effect of the atmosphere of growth is incompletely understood, and older *N. gonorrhoeae* cultures will grow without the addition of carbon dioxide, an atmosphere of between 5 and 100 carbon dioxide together with 90 to 95% air has been found highly suitable.

After the initial inoculation, the plate is covered with from about 50 to about 75% growth, the growth is removed therefrom. In a suitable procedure, a small amount of sterile casamino acids solution is added to the inoculum plate and the growth scraped off with a sterile glass spreader. It has been found suitable to utilize between 5 and 6 ml. of solution suitably about 0.7% by weight per plate and from 2 to 3 ml. of the thus prepared suspension is sufficient to inoculate the larger growth pans of GC medium. The pans are then incubated for the same order of time under the same conditions as the inoculum petri dishes and the pili harvested therefrom.

At this point of the procedure it is no longer necessary to utilize sterile techniques although of course as in all procedures, it is desirable to use clean equipment, pure reagents, and to carry out all operations at as low a temperature as possible to inhibit undesired bacterial growth.

The gonococcal growth is harvested using a suitable buffer. While the chemical nature of the buffer is not critical, the pH range is important. For reasons which will become apparent, when purifying $T_2$ pili the buffer may not be utilized at a range exceeding pH 9.3. It is preferred to operate in a pH range between 3.5 and 9.2, most suitably in a range of 7.0 to 8.6. Where a predominantly $T_1$ culture has been employed the pH should not exceed 7.7, but should lie in the range of pH 5.5–7.5, suitably pH 7.0–7.2. These ranges will ensure the maintenance of all piliated material in the aggregated state. As the most suitable buffer, may be mentioned tris buffered saline.

In the preferred procedure the washing buffer is placed on the surface of the growth medium, the growth scraped off the medium with a suitable instrument, and the aqueous suspension removed in a suitable manner, for example, with a pipette or vacuum aspirator. If desired, a second washing may be carried out in the same manner and the liquid suspensions pooled.

In order to raise the yield a third washing may be carried out with a high pH buffer. That is to say, a buffer having a pH above 9.3, suitably between 10.1 and 10.3. The use of such a buffer will cause dissolution of all remaining pilic material. Where $T_1$ pilus isolation is in view, the pH need only exceed about pH 8.6, but there is no disadvantage in the higher values. This basic suspension is not pooled with the first washes but held aside for a later stage of the purification. It should be noted that where there has been a good growth of pili, the growth has a characteristic orange/pink or warm pink color and the growth medium has an odor resembling cooking food. The growth is noted to be clumped together in sticky ropey aggregates and slides easily off the growth medium when pushed with a suitable instrument, such as a glass spreader.

While the foregoing procedures are desirable where high yields of high purity pili are in view, quite acceptable results are obtainable by a substantially abbreviated procedure. In this procedure the first and second wash procedures set forth above are not utilized. The entire growth is treated with substantially elevated pH buffer suitably an ethanolamine buffer in accordance with the procedures of the third washing. The wash medium will contain, in addition to the dissolved pili, many impurities otherwise removed, however, it has been found that these impurities may be held in solution upon precipitation of the pilic material in the manner discussed below.

Deep Culture of *N. gonorrhoeae* Organisms

The deep culture of the organisms of type $T_1$ and $T_2$ in liquid medium is carried out in a conventional manner utilizing a medium and environment identical to that used for the surface culture except that the medium does not contain agar as a solidifying agent. It has been noted that the organisms grow and shuck pili continuously. Thus, a deep culture medium will contain much suspended pilic material. Where type $T_2$ cultures are being grown the pH, being normally below pH 9.3, there is no undesired solubilization of the pili. In the culture of $T_1$ organisms the pH may rise above pH 7.7, hence prior to work-up as described hereinbelow, the pH should be adjusted down into the range of 5.5–7.7, preferably to about pH 7.0–pH 7.2. While it is not critical, it is preferred to make such an adjustment a few hours, say 8–20 hours before work-up to ensure crystallization of partially solubilized $T_1$ pili.

In both $T_1$ and $T_2$ cultures, it is helpful, but by no means essential to carry out the growth in a mildly agitated medium in the presence of a small amount of diatomaceous earth such as Celite. The amount of, say, Celite should suitably be between about 0.1 and about 0.5%, suitably about 0.3% by weight of the growth medium.

Purification of Pili

Separation of pilus crystals from growth medium

It should be noted that the wash from the surface growth of the *N. gonorrhoeae* organisms contains material soluble therein which is of no interest in the isolation of GC pilus crystals. Similarly, the same is true of the deep growth liquid cultures. In the case of the surface growth wash (first two washes only), the amount of liquid relative to the amount of growth is relatively small. It is preferred to centrifuge the entire wash material at relatively low speeds. The speed of centrifugation and the time of spin down is by no means critical. However, it has been found helpful to spin at between about 1000 G and 12,000 G (hereinafter written as 1 KG and 12 KG), for from about 5 to about 30 minutes, preferably at about 3 KG for from about 10 to about 15 minutes. The residue in the pellet contains both cellular, and pilic material, both of which are retained at this stage and the supernatant is discarded. The supernatant contains substantial amounts of impurities as well as small amounts of pili which are not worth recovering.

Where deep growth is the mode of the culture utilized, the volume of liquid is rather substantial and therefore centrifugation may be somewhat cumbersome. The use of a diatomaceous earth sandwich filter has been found useful in concentrating the growth from deepth cultures. In this procedure a very coarse filter paper is laid on the filter pad, suitably a sintered glass or Buchner type surface, a layer of diatomaceous earth, suitably Celite of about 2 to about 5 mm thickness is charged thereon and covered with a second coarse filter paper. The Celite serves as the actual filtration medium while the upper filter paper serves merely to preserve the surface. The culture broth, having been checked for pH to ensure the pili are present in crystalline form is filtered through the filter pad and the filtrate discarded. The combined residues are then taken up in say, a high pH buffer similar to that utilized for the third wash of the surface growth culture, and this suspension is centrifuged at from about 1 KG to about 12 KG. It should be noted of course that in this case the pellet will contain the diatomaceous earth carrier and cell debris, and the pilic material will be in the supernatant.

It is desirable at this point to separate the GC pilus material from the cell debris and, in the case of the deep growth culture, the diatomaceous earth as well.

In the case of the surface culture pellet centrifuged from the low pH wash, this may be done by adding an aqueous medium which will break the noncovalent bonds between pilus rods in the system while leaving the covalent bonds intact thus dissolving the pilus crystals to give solubilized single rod pili. Such a medium may require raising the pH or may permit the pH to be unchanged. Where solubilization is to be carried out by pH change, there is added to the residue a suitable, moderately high pH buffer. It is desirable that the buffer have a pH of between 9.3 and 11, preferably between pH 10.0 and pH 10.4. With higher pH's there is a risk of denaturation of the peptides. This level of pH will solubilize $T_1$ and $T_2$ pilus crystals.

Where it is desired to separate $T_1$ from $T_2$ pili in the original solid pellet, the pH of the buffer is initially provided to be greater than about pH 7.7 but less than about pH 9.3. The suspension is then centrifuged and the supernatant therefrom can then be set aside or discarded according to the needs of the procedure. If the original solid pellet was believed to have contained substantial amounts of type $T_2$ pili, fresh buffer of higher pH, namely above about pH 9.3 is added which will provide a solvent phase containing said $T_2$ pili but free of type $T_1$ pili. The actual composition of the buffer utilized at this stage is not critical, howeveer, a tris-saline buffer is especially preferred.

In both of the foregoing modifications, there is added to the total solids a volume of buffer approximately equal to 3 times the volume of the solids. Again, this amount is not critical but has been found to be sufficient to dissolve the pilic material without utilizing excessive volumes of the aqueous medium. If the pili are from a surface culture and said surface culture was subjected to a third stage high pH wash with a similar buffer, this wash may be added at this point. The pellet is then suspended in the aqueous medium. The method of bringing the pellet into suspension is not critical, short gentle sonication, long magnetic stirring, hand pipetting, hand mixing, vortexing or mechanical stirring may be used.

It has been found preferable to utilize mechanical stirring for a few seconds. While the mode of suspension is not critical, it is important that whatever mode is utilized the cells are not ruptured since cell rutpure will introduce undesired material into the aqueous layer. The occurrence of cell rupture is noted as a layered pellet of pink above white in the subsequent centrifugation. The suspended material is then centrifuged. The manner of centrifugation is not critical, however, the conditions set forth above for the first centrifugation step have been found suitable. Filtration may be used in place of centrifugation.

The dissolved pili are found in the supernatant or filtrate from which they may be precipitated upon lowering of the pH. The degree of pH lowering will of course depend on whether type $T_1$ or $T_2$ pili are in process. Alternately precipitation may be achieved by adding sufficient ammonium salt, suitably a mineral acid salt such as the sulfate, preferably as an aqueous solution, to provide an ammonium sulfate, concentration of between about 4% saturation to about 10% saturation. However, in order to increase the yield and increase the degree of purity, it has been found desirable to introduce intermediate steps prior to the precipitation.

In carrying out these additional yield and purification steps, the supernatant and the pellet from the high pH centrifugation or filtration are both retained. The pellet from the high pH centrifugation stage is re-suspended, suitably in the same aqueous medium at the same pH in the same manner and the suspension centrifuged again in the same manner. After this centrifugation, the pellet is discarded and the supernatant from both high pH centrifugations are combined and recentrifuged.

The purpose of the recentrifugation is to remove residual suspended impurities. Centrifugation is therefore carried out at a higher speed than heretofore. Speeds from between 12 KG and 70 KG for from about 30 to about 60 minutes are operative. It is generally preferred however to spin at from about 27 KG to about 40 KG for about 60 minutes. The pellets are discarded and the supernatant retained.

At this stage it is usually desirable to sterilize the pilus solution. This is required by certain FDA rules for certain purposes. Such sterilization may be readily achieved by passing the pilus solution, immediately before precipitation, thru a millipore filter, a 0.45 micron filter has been found especially suitable. Thereafter of course the materials must be handled in an aseptic manner, if it is desired to maintain sterility.

Under certain circumstances it may be desirable to isolate the pili in individual rod form rather than in crystal form. In this case the supernatant is respun in an ultra high speed centrifuge at between 60 and 166, suitably 106 KG for between 2 and 4 hours, whereby the pili are pelleted in individual rod form.

The pili are re-precipitated by lowering the pH of the supernatant to below 9.1. It has been found that the best results in terms of the nature of the crystalline material have been obtained by dialysis against a suitable low pH buffer. It has been found desirable to utilize a buffer having an initial pH of between 8.3 and 8.6, for $T_2$ pili, while the chemical nature of the buffer is not critical, tris buffered saline has been found suitable. Dialysis is suitably carried out utilizing an excess of between about 30 and about 60 fold, suitably about 40 fold. The dialysis is carried out with magnetic stirring of the external dialyzing medium for a period of from about 12 to about 18 hours. It is preferred to carry out the dialysis at a reduced temperature, that is to say, an ambient temperature of from about 0° to about 10° C. This lower temperature range lowers the incidence of undesired bacterial contamination. It should also be noted that the buffer pH is temperature dependent. Hence, if the temperature of the buffer is measured after the system has cooled down to its operating temperature, the pH may be found to have risen as high as pH 9.1. However, satisfactory results are still obtained. It should further be noted that it is not generally necessary to change the buffer where excess buffer in the range stated herein is utilized. The crystal suspension is then processed to separate the pilus crystals. Most suitably separation is carried out by moderate speed centrifugation. Centrifugation at from about 3 KG to about 8 KG for about 60 minutes has been found suitable. The supernatant is then discarded.

Where it is desired to purify the pilus crystals further, the cycle of solution-high speed centrifugation-dialysis-recentrifugation may be repeated two or three times.

If the pilus crystals are not to be utilized immediately, notwithstanding sterilization by filtration, the addition of preservative has been found helpful. It is desirable that the preservative be added not to the pilus crystals themselves or to a solution containing them, but rather to the dialysis buffer utilized to lower the pH of the solution. In the event that the added preservative is incompatible with the buffer, then, after crystallization of the pilus crystals has occurred, the incompatible buffer may be removed by dialysis against a compatible buffer and a further dialysis carried out utilizing the preservative plus the new buffer. Among the preservatives that may be used are formaldehyde, merthiolate and azide. There are used between about 0.02 and about 0.05% of these preservatives.

Each of the named preservatives has certain detrimental effects. Formaldehyde causes cross-linking between the pilus rods. They may thus not be redissolved as before. Merthiolate has no cross-linking effect and the crystals may be reformed, however, such reformed crystals have a decreased ability to agglutinate in the presence of antibodies to the pili. Nevertheless, the antigenicity is not affected. That is to say, when injected into test subjects they cause the formation of apparently normal antibodies to the pili. Azide is a very satisfactory preservative in that it affects neither crystal structure nor antigenicity nor agglutination. Unfortunately, it is toxic and cannot be employed where injection of the pilus crystals into human subjects is contemplated. The crystal preparation is suitably stored at low temperatures, i.e. at about 1° C. to 4° C. However, where long storage is contemplated it is preferable to dissolve the crystals in an appropriate high pH buffer, filter thru a millipore filter and store in solution under sterile conditions. When the pili are required in crystalline form it is preferable to reconstitute them by lowering the pH to the appropriate crystallization value for $T_1$ or $T_2$ pili as the case may be. Both sterilization and a preservative can be employed when it is desired to achieve the best possible conditions of preservation.

Purification of Pili by Constant pH Dissolution

The technique utilized to purify pili at constant pH is substantially similar to that utilized hereinabove using different pH levels.

As solubilizing agents there may be utilized aqueous solutions of, for example, salts, suitably salts of alkali, and alkaline earth metals with the anions of mineral acids, at an ionic strength above 0.5, suitably between about 4.0 and about 5.0, preferably about 4.4, urea at a concentration of between 3M and about 5M sucrose above a concentration of 50% by weight and finally water itself where the ionic strength of the solution is reduced below 0.002M.

In one modification of this embodiment of the invention instead of suspending the first centrifugate pellet which comprises cells, pili, and debris, in a high pH medium, there is utilized in place thereof any of the foregoing agents in the environments aforesaid. The suspension is then low speed centrifuged as before. If higher yield is desired the supernatant from the low speed centrifugation is set aside, pellets resuspended in a similar medium, recentrifuged and the thus produced supernatant combined with the previous supernate and high speed centrifuged. Pellets from high speed centrifugation are discarded and the supernatant dialyzed against a suitable buffer to remove the solvating medium.

Thus, where solvating agent is a high concentration salt or sucrose, the ionic strength is reduced to below 0.5 for the salt and below 40% for the sucrose. In the case of urea, the urea is dialyzed against a suitable buffer, say, tris buffered saline, to provide ionic strength of between 0.05 and 0.3 at pH 7.0 or pH 8.3, depending on whether $T_1$ or $T_2$ pili are being processed, similarly when the solvating agent is water similar procedures are used to raise the ionic strength to at least 0.05.

The buffers utilized for this purpose are the same as the buffers utilized in the differential pH purification method and, moreover, are utilized in the same manner.

Purification of GC Pili by Density Gradient Centrifugation

Density gradient centrifugation is carried out by subjecting a mixture of pili and aqueous caesium chloride to centrifugation together and the optical density at a given wave length utilized to indicate the portion of the tube containing the pili.

While centrifugation may be carried out at a pH under pH 9, better results are obtained by carrying out the centrifugation in the pH range of 10.0 to 10.4, suitably at pH 10.1. In this procedure, the crude pellet containing cellular materials, pili, and debris, is suspended in a high pH buffer, as set forth hereinabove, and a suitable quantity of caesium chloride added thereto. For example, it has been found suitable to prepare a medium containing from about 2 to about 5 grams of dry caesium chloride per 10 ml. of aqueous medium. Thus, it has been found most suitable to utilize about 7.5 grams of caesium chloride to 20 ml. of aqueous medium.

The mixture is then spun at from about 110 to about 250 KG, suitably about 200 KG for from about 30 to about 60 hours, suitably for about 42 hours and the optical density of fractions at a given point in the tube measured. Optical density measurements at 280 nm show a single peak. The density fractions under this peak are separated and dialyzed against a low pH buffer to form the pilus crystals in the same manner as that set forth hereinabove. The actual density range of the solution fractions collected at this point at 20° C. is between 1.35 to 1.33 at pH 10.1.

PAT Test for *N. Gonorrhoeae* Antibodies

The basic ability of GC pilus crystals or single pilus rods to agglutinate in the presence of antibodies to *N. gonorrhoeae* is the basis of the PAT Test. In this test, sera from the blood of subjects suspected of having been exposed to *N. gonorrhoeae* are mixed with GC pilus crystals or single pilus rods and the mixture observed for agglutination of the crystals or the rods.

In order for this test to be evaluated in its true light, three important factors must be considered. First, the test is not intended to replace the standard "culture" test but may serve as a screen to determine exposure to *N. gonorrhoeae*. The test will therefore show positive for both subjects who have had an active infection for more than a few days and also for subjects who have been exposed to the disease but have since been cured. The third caveat is that very recently infected subjects may not have developed enough antibodies to give a positive reading. Subjects showing a positive result in the test should be subject to the traditional culture test. It has been found as will be discussed further hereinbelow, that the pili of infectious forms of *N. gonorrhoeae* possess a number of specific immunologic determinants. Pili of certain strains will possess one or more of these determinants. Hence, for a screen to be effective, it must be carried out using pilus crystals which cover the spectrum of immunologic determinants.

The GC pilus crystals utilized in the test are prepared in the manner set forth hereinabove.

The test may be carried out using either serum or plasma from the test subject. References herein to serum or plasma therefore can be considered interchangeable for purposes of the test. The amount of serum or plasma required is extremely small. It has been found satisfactory to puncture the subjects finger to obtain a few drops of blood and to spin these down in a small (circa 250 μl) centrifuge tube to yield between 10 and 20 μl of plasma which are adequate for carrying out the test.

It is customary to carry out tests of this nature at various levels of dilution. The serum is therefore diluted in predetermined (usually serial dilutions) with a predetermined suitable diluent. The nature of the diluent is not critical provided that it does not interfere with the operation of the test. Any aqueous buffer such as phosphate buffered saline or tris buffered saline having a pH of between 7.0 and 7.5 may be utilized. Tris buffered saline having a pH of 7.2 is preferred. In the operation of the test, pilus suspension is added to the diluted serum to give a final concentration of between 10 and 50 micrograms per ml. of crystals in the suspension. It has been found that the best results are obtained at the lower concentration of pilus crystals, hence, for purposes of standardization of pilus antibody levels in test sera, the arbitrary concentration for comparison purposes of 20 micrograms of pilus crystals per ml. of diluted serum (or plasma) have been taken as the standard.

After mixing the pilus crystals with the diluted sera, the mixture is incubated. The time of incubation is not critical and may be from as little as 15 minutes to as long as 48 hours with negligible change in the reading. In a rapid form of the PAT Test the serum-pilus mixture is agitated on a slide by hand for 1 to 3 minutes, similar results are obtained but with some loss in sensitivity. The temperature at which the mixture is maintained is also not significant as long as it is maintained between 0° and about 45° except that it appears preferable to maintain the mixture at a temperature of between 22° C. and 40° C., suitable at about 22° for at least 15 minutes. Storage of the mixture thereafter at temperatures as low as 4° C. for up to 24 hours do not appear to give significant changes of titer. Satisfactory results have been obtained by incubation for 30 minutes at 37° C. At the expiration of the incubation period an aliquot is placed under a dark field microscope and the agglutination noted and scored. The scoring is done in the usual arbitrary relative way for tests of this nature, namely, 4+, 3+, 2+, 1+, =±and −. In determining the titer of a given sample the last dilution which gives a 1+ agglutination is taken as the final reading. The 1+ score is that score which shows the minimal noticeable agglutination over a standard control sample.

Since the titer readings may vary from batch to batch of pilus crystals according to their condition it is advisable to monitor the test, when carried out, by running the crystals against antisera of known PAT titer in addition to the usual controls against diluent without serum, and diluent with normal serum.

It has been found that under the conditions utilized, the test is reproduciable within a titer reading of a times 2 (×2) factor.

Serotyping of *N. Gonorrhoeae*

Heretofore, it has not been possible to serotype *N. gonorrhoeae* organisms into a useful and meaningful system. It is not unusual for organisms of different strains of the same species to call forth different antibody responses. These antibody responses characterize the strains and identification of these characteristics constitutes a substantial aid in epidemiological studies of the progress and origin of a particular outbreak of the disease. It is particularly of interest in the venereal diseases since the elimination of the disease very often depends upon person-to-person contact tracking. Thus, if the source of an infection can be identified by serotyping, this type of tracking can be greatly assisted.

It has been found that by examination of 21 strains derived from sources well distributed throughout the United States that there are at least four (4) immunological determinants present in the pili of these strains. One or more of these determinants are present in each strain. Hence, if the determinant characteristics of a particular sample can be identified the origin of the infection can be more readily discovered.

Where *N. gonorrhoeae* organisms are derived from an infected subject and grown to produce pilus crystals the immunologic determinants present in the pilus crystals from the subject may be readily discovered by subjecting them to the PAT Test with the aforementioned typing sera which are known to contain antibodies for but one determinant. Thus, the serological profile of any given sample organism may be established.

Gonorrhoeae Vaccine—Safety and Potency

G. C. Pilus crystals and single rod pili have been injected into test subjects in vivo and found to have no toxic effect whatsoever. The only negative effects were noted with intravenously injected chick embryoes. Test rabbits were given three (3) injections subcutaneously of 100 to 200 micrograms per Kg, giving a total dosage of 300 to 600 micrograms per Kg, rats were similarly injected two (2) times at 8,000 micrograms per Kg, giving a total dosage of 16,000 micrograms per Kg. Rhesus monkeys received three (3) injections of 100 micrograms per Kg intramuscularly, and humans received injections of 2–10 micrograms per Kg, followed by one (1) injection of 50 micrograms per Kg intramuscularly. None of the test animals died nor showed any local or systemic toxic effects, the chick embryos showed an LD-50 of 60 micrograms per pound. The reactions in human subjects varied from no systemic effects whatsoever to transient chills and fever in one of the subjects tested. The PAT titer in rabbits reached 1,000 to 8,000, and in Rhesus monkeys reached 10,000+. The PAT titer in humans varied between 100 and 200.

The dose required to infect 50% of test subjects ($ID_{50}$) is of the order of $5.0 \times 10^2$ organisms. Preliminary experiments indicate that the $ID_{50}$ of a human subject having a PAT titer of 100–200 is $2.0 \times 10^4$ organisms. This represents 1.6 log cycles of protection, or stated another way, a human subject having a PAT titer of 100–200 has only about a 0.86% chance of being infected after I contact whereas an unimmunized person runs about a 30% risk.

In view of these findings, in order to provide an acceptable level of protection in humans, the human subject should have administered a sufficient quantity of GC pilus crystals suitably against all known determinant factors to raise the PAT level against each of these determinants to at least 100, preferably to at least 200. Such levels are obtainable by administering between from about 2 to about 100 micrograms per kilogram body weight of GC pilus crystals of each determinant. It should be noted however, that a titre of 100 is achievable with as little as 1 $\mu g$/Kg. The mode of administration will depend upon the sensitivity, if any, of the subject, buy may suitably be administered in between 1 and 5 doses over a time period of up to 8 weeks.

The GC pilus crystals, single pilus rods, or other sources of GC pilin may be administered in any suitable medium for intramuscular injection.

EXPERIMENTAL

Sources of *N. Gonorrhoeae* Utilized 21 strains of *N. gonorrhoeae* were isolated from humans with Gonorrhoeae and are designated as follows:

| | | |
|---|---|---|
| Pittsburgh 1-2 | CDC M-2 | Seattle 1-2 |
| Pittsburgh 3-2 | CDC T-2 | Seattle 3-2 |
| Pittsburgh 4-2 | CDC F62-2 | Seattle 9-2 |
| Pittsburgh 6-2 | Atlanta 4-2 | Norfolk 2-2 |
| Pittsburgh 7-2 | Atlanta 6-2 | Norfolk 7-2 |
| CDC 8-2 | Atlanta 9-2 | Dayton 8-2 |
| CDC 0-2 | Atlanta 10-2 | CDC 005-2 |

In all of the following Examples, specific reference is made to the Pittsburgh 3-2 strain. When the other named organisms are subjected to the same procedures, as the Pittsburgh 3-2 strain, similar results are obtained.

EXAMPLE I

Strain Purification

The primary cultures of the Pittsburgh 3-2 strain were plated out on Thayer-Martin plates containing Thayer-Martin Agar (Manual of Clinical Microbiology, 2nd. Ed., Amer. Soc. Microbiol, Lenette, et al. (Ed.) 1974, p. 920). The plates are incubated for about 18 hours at 35° C. in a humidity of 90% in an atmosphere comprising 95% air and 5% carbon dioxide. The plates are inspected and colonies resembling the highly piliated $T_2$ form are re-streaked on GC medium. After incubation under the above conditions the $T_2$ type colonies are picked and restreaked again on GC medium.

In accordance with the above procedure, but where the culture of the $T_1$ type of this organism is desired colonies having a preponderance of the less piliated $T_1$ type are similarly restreaked.

EXAMPLE II

Preparation of GC Growth Medium (a) Preparation of DSF Supplement

An aqueous solution of cocarboxylase (0.2% by weight) in distilled water is prepared at ambient temperature and sterilized by filtration through a 0.45 micron millipore filter. An aqueous solution comprising glucose (40 g.), glutamine (1.0 g.), ferric nitrate (0.5% by weight, 10 ml. in distilled water), and distilled water (90 ml.) are heated in an autoclave at 121° C. with 16 psi pressure for 10 minutes and the solution cooled. To this autoclaved solution is added 1 ml. of the previously prepared cocarboxylase solution to provide the DSF solution.

(b) Preparation of Growth Medium

Bacto GC Medium Base (Difco Mannual 19th. Ed., p. 122) (Difco Laboratories, Detroit, Michigan) (10.8 g.) and distilled water (300 ml.) are gently agitated in a suitable container and the mixture in the container autoclaved at 121° C. with 16 psi pressure for 15 minutes. The container is removed from the autoclave, cooled to between 50° C. and 60° C. and the DSF supplement, prepared as above, (3 ml.) is added thereto.

Preparation of Inoculum Plates and Growth Dishes

Pyrex or aluminum growth dishes and petri type inoculum dishes are washed, rinsed in distilled water, covered with aluminum foil, and autoclaved for 30 minutes at 121° C. with 16 psi pressure. Into the thus prepared dishes is poured the molten growth medium prepared as above in Example II. The plates should be poured with care in a closed dust free room utilizing aseptic techniques to prevent contamination with undesired bacteria.

EXAMPLE III

Growth of Inoculum

The T-2 colonies from the Thayer-Martin plates (Example I) are re-streaked on inoculum plates prepared as above and cultured at 35°, 90% humidity, in an atmosphere of 5% carbon dioxide and 95% air. The plates are progressively subcultured until more than 90% of the growth is the piliated $T_2$ colonial type. Depending upon the stability of the strain the growth time is between 12 and 24 hours, at which time the plate will be covered with between 50% and 75% of growth.

EXAMPLE IV

Production of GC Pili by Surface Culture

The petri dishes of Example III containing the $T_2$ growth are washed with aqueous casamino acid solution (5 ml, 0.7% by weight). The growth is scraped off the medium with a sterile glass spreader, the suspension of the growth in the casamino acid solution is pipetted from the plate and divided between two (2) growth pans ca. (14×10 in). Said pans having been prepared in the manner set forth above. The suspension is spread evenly over the surface and the pans incubated at 35° C., 90% humidity, in 5% carbon dioxide plus 95% air atmosphere for 20 hours.

Harvesting of Surface Culture Growth

A stock solution of tris buffered saline is prepared by dissolving sodium chloride (510 g.), tris, also known as tris(hydroxymethyl)aminomethane (363 g.) and concentrated hydrochloric acid (100 ml.), together with distilled water sufficient to produce a stock solution having a volume of 10 liters. The pH is adjusted to a standard working pH of pH 8.5 by the addition of more concentrated hydrochloric acid. Where an upward pH adjustment is required, concentrated (10N) aqueous sodium hydroxide is added. Prior to use the stock solution is diluted to 1/6 of the original concentration. The tris buffered saline (hereinafter TBS) has an initial pH of 8.5. 10 ml. of the TBS solution is placed on the growth surface of the production pan, the growth scraped off with a glass scraper and the suspension pipetted off into a reservoir. The washing and scraping is repeated with a second batch of TBS (10 ml.), and both washings pooled. The growth surface is washed a third time with ethanolamine buffer (10 ml., pH 10.1) and the suspension retained but not pooled. (The ethanolamine buffer is prepared from liquid ethanolamine, 37.3 ml., aqueous hydrochloric acid, 1M, 147.0 ml. and distilled water to 1 liter).

In accordance with the above procedure, where $T_1$ rather than $T_2$ pili are being cultured the pH of the TBS is between pH 7.0 and 7.2.

In a good production run the growth has a characteristic orange/pink or warm pink color and an odor resembling cooking food. The growth clumps together in sticky ropy aggregates and slides readily off the agar surface of the medium when pushed with a glass spreader.

The pans containing the growth medium are then cleaned, washed and sterilized in the manner set forth above, and recharged with more growth medium.

EXAMPLE V

Deep Culture Growth of G. C. Pili

In accordance with the procedures of Example IV using the same growth medium and nutrient supplement but excluding the again and substituting soluble starch for the insoluble starch, inoculum is charged to the growth medium and incubated in an atmosphere of 95% air and 5% $CO_2$ at 35°–37° C. in the presence of up to 0.5% (based on volume of liquid medium) of Celite, for 18 hours under gentle agitation.

The culture medium is then filtered thru a sandwich filter pad on a coarse sintered glass funnel. The filter pad comprises a coarse filter paper, a 5 mm layer of Celite and a further coarse filter paper.

The filtrate is discarded and the residue treated in accordance with the third (ethanolamine buffer) wash procedure of Example IV, which is then processed in accordance with the procedures of Example VI, paragraph iii, infra et seq.

EXAMPLE VI

Separation of Pili from Cells and Debris (i) The TBS suspensions produced in the foregoing Examples are charged to centrifuge tubes (volume of the tubes depending on the number of production runs combined) and centrifuged for 15 minutes at 3 KG. The supernatant is discarded and the pellet retained.

(ii) To the pellet is added the ethanolamine suspension from the third wash of the growth pan and additional ethanolamine buffer at pH 10.1 to a volume approximately 3 times the observed pellet volume in the centrifuge tube. The liquid layer is stirred rapidly for 5 seconds with a mechanical stirrer to bring the soluble portion of pelleted material into suspension.

(iii) The suspension is then centrifuged for 15 minutes at 3 KG the supernatant decanted from the pellet and preserved. The pellet is then resuspended in 3 times its volume of ethanolamine buffer pH 10.1 as hereinabove, and recentrifuged for 15 minutes at 3 KG. The supernatant is decanted and pooled with the ethanolamine buffer supernatant from the immediately prior step and the pellet discarded.

The combined ethanolamine buffer supernatant are centrifuged at 31 KG for 60 minutes. The supernatant is decanted and preserved and the pellet discarded.

EXAMPLE VII

Crystallization of GC Pili

Preparation of Dialysis Tubing and Tris Buffered Saline

A roll of dialysis tubing (100 foot, Fisher Scientific Catalog Number 8-677 B) is boiled sequentially in a) distilled water (2X, 4 liters each time), b) aqueous sodium bicarbonate (2X, distilled water, 4 liters, containing sodium bicarbonate 2 teaspoons each wash), c) aqueous disodium ethylene diamine tetraacetate (2X, distilled water, 4 liters, Na EDTA 2 teaspoons: each time), d) aqueous ethanol (2X, ethanol/water, 1:1, 4 liters: each time), e) distilled water (2X, 4 liters, each time). The dialysis tubing is then stored in distilled water containing a trace of benzoic acid (distilled water 4 liters, benzoic acid 1 teaspoon). Tris buffered saline stock (TBS) prepared in accordance with Example IV is diluted with distilled water to provide the dialysis solution (166 ml. stock solution diluted to 1 liter with distilled water).

Dialysis of GC Pili Solution 100 ml. of ethanolamine buffer containing GC Pili in solution as produced in the foregoing Example are dialyzed against 4 liters of TBS (pH 8.5 measured at 20° C.) utilizing dialysis tubing prepared as above and utilizing diluted TBS as prepared above. The dialysis is carried out in a cold room (ambient temperature circa 4° C.). The external dialysis buffer solution is stirred magnetically. Dialysis is carried out for 18 hours. A rise to pH circa 8.7 in the dialysis medium is noted. A cloudy blue/white birefringent precipitate of GC pilus crystals is formed at the end of the dialysis period. The thus precipitated material is centrifuged at 7.5 Krpm for 60 minutes and the supernatant discarded to leave GC pilus crystals of Pittsburgh strain 3-2 $N.$ $gonorrhoeae$ as the pellet. In accordance with the above procedures, but where $T_1$ rather than $T_2$ pili are to be isolated, the initial pH of the TBS is pH 7.0-7.2.

EXAMPLE VIII

Further Purification of Pili

The pellet of Example VII is suspended in approximately 30 times its volume of ethanolamine buffer (pH 10.1). The tubes swirled gently to dissolve the pellet and the suspension centrifuged for 60 minutes at 31 KG. The supernatant is decanted off and the pellet discarded. The supernate is dialyzed against TBS in accordance with the procedure of Example VII, and the thus obtained crystalline material isolated by centrifugation also in accordance with the procedures of Example VII. The pellet is once more resuspended in ethanolamine in accordance with the foregoing procedures, filtered through a 0.45 micron filter if sterilization is desired and similarly recentrifuged and redialyzed as hereto ore, and, similarly, isolated by centrifugation.

In accordance with the foregoing procedures, where the thus formed GC pilus crystals are to be stored for a moderate period of time, a preservative is added to the dialyzing TBS solution where the preservative is compatible therewith. Compatible preservatives which may be utilized in accordance with this procedure are 0.05% weight per volume of neutral aqueous formaldehyde, 0.01% weight per volume merthiolate or 0.02% weight per volume sodium azide.

In accordance with the foregoing procedure where the preservative is not compatible with TBS after the Pili· have crystallized, the tris buffer is removed by dialysis against saline (0.15M aqueous sodium chloride, 18 hours). The preservative is added to a fresh batch of said saline, and dialyzed against the suspension of GC pilus crystals for 18 hours. The crystals are stored in this medium at 40° C. Alternatively the medium containing the crystals may be frozen and stored at −70° C.

Yield

The yield of GC pilus crystals from the strains of $N.$ $gonorrhoeae$ listed in Example I, where the inocula contain at least 90% $T_2$ colonial types, lies in the range of 5 to 15 micrograms/square centimeter of growth surface.

Similar but slightly lower yields are obtained from $T_1$ colonial types.

EXAMPLE IX

Caesium Chloride Density Gradient Isolation of GC Pili 1 ml. of the TBS (pH 8.5) wash containing GC pilus crystal suspension from Example VI is diluted to 20 ml. with tris pH 8.5 buffer, the pH adjusted to pH 10.1 by the addition of aqueous sodium hydroxide (0.1N) and 7.5 grams of dry caesium chloride added thereto. The solution is spun at 200 KG in the SW41 Rotor of a Beckman L-265 Centrifuge for 42 hours. Fractions are collected from the tube and the optical density at 28 nm and the refractive index for each sample measured. The refractive index is related to caesium chloride density to which the refractive index readings are converted. The fraction number is plotted on the X axis against solution density on one Y axis and optical density on a second Y axis. A single principal peak corresponding to the GC pili is located at equals 1.3422±0.0038. The fractions whose equals 1.35 to 1.33 are combined and dialyzed and purified to yield GC pilus crystals in accordance with the procedures of Examples VII through VIII.

EXAMPLE X

Gel Electrophoresis of GC Pili (Method of Ornstein and Davis-Disc Electrophoresis 1962-Distillation Products Industries, Rochester, N.Y.)

Standard cylinders of 10% acrylamide gel (9.7% acrylamide and 0.3% N,N'-methylene-bis-acrylogo there merized with TEMED) and ammonium persulfate were prepared and set up between gel and reservoir buffers comprising tris hydrochloride at pH 8.0 and 0.1% SDS. The upper gel surface was loaded with a charge comprising 50 micrograms of $T_2$ pilus crystals, 20 ug of Clelands Reagent (0.01M) 1 mg. of SDS 20λ of glycol and 20λ of Bromophenol Blue (0.002%). Prior to charge the pili were heated with the SDS and the Cleland's reagent for 2 minutes at 100° C. The electrophoresis was run at 5 ma (at ca. 170 v) until the Bromophenol Blue had run 6 cm. The gels were removed and cut thru the dye band and two gels stained with Coomassie Blue Stain (0.2%) to give two bands—a major band and a minor band.

The unstained gels were frozen and bands corresponding in position to the stained bands were cut out.

The major band was extracted with reservoir buffer at 37° C. in a rotator for 24 hours, the buffer drawn off and evaporated almost to dryness. A rerun of the product yielded a single band of the same Rf value. This material is designated GC pilin.

Antigenicity Test of G.C. Pilin

The gel containing the major band was homogenized with about 10 ml. of saline and injected into three test rabbits subcutaneously. Test animals $P_I$ and $P_{II}$ received 3.1 ml suspension and $P_{III}$ only 2 ml. of the suspension.

Second and third injections were made about 15 and about 30 days later. The materials of the second and third injections were prepared by extracting the major protein into reservoir buffer (0.8 ml.) at 37° C. for 24 hours. The extracted buffer was then combined with an equal volume of Freund's Incomplete adjuvant and one-third of each mixture injected into each rabbit.

One week after the last injection all rabbits showed titres exceeding 1000 in the PAT Test against Pittsburg 3-2 Type $T_2$ pili as shown in the Table below.

| | PCA TEST USING 50 Y/ml "3-2" PILI | | | | | | | | Pre-immune Rabbit |
|---|---|---|---|---|---|---|---|---|---|
| Rabbit | PI | PI | PI | PII | PII | PII | PIII | PIII | PIII | |
| Bled: Day # | 1 | 15 | 29 | 1 | 15 | 29 | 1 | 15 | 29 | −204 |
| Test Done | 16 | 16 | 35 | 16 | 16 | 35 | 16 | 16 | 35 | 35 |
| Dilution | | | | | | | | | | |
| 1/2 | ± | +/++ | 3+ | 3+ | 3+ | 4+ | ± | ++ | 3+ | 0 |
| 1/4 | ± | + | 3+ | 3+ | 5+ | 5+ | 0 | 3+ | 3+ | 0 |
| 1/8 | 0 | ± | 3+ | 3+ | 5+ | 5+ | 0 | 3+ | 4+ | 0 |
| 1/16 | 0 | 0 | 3+ | 3+ | 5+ | 4+ | 0 | ++ | 4+ | 0 |
| 1/32 | 0 | 0 | 3+ | + | 4+ | 4+ | 0 | ± | 4+ | 0 |
| 1/64 | 0 | 0 | + | 0 | 4+ | 3+ | 0 | 0 | 0 | 0 |
| 1/128 | 0 | 0 | + | 0 | 4+ | 3+ | 0 | 0 | ++ | 0 |
| 1/256 | | | + | | | 3+ | | | + | 0 |
| 1/512 | | | + | | | ++ | | | ± | 0 |
| 1/1024 | | | + | | | ++ | | | + | 0 |
| 1/2048 | | | 0 | | | + | | | + | 0 |
| 1/4096 | | | 0 | | | + | | | 0 | 0 |
| end point | <2 | 4 | 1024 | 32 | >128 | >4096 | <2 | 16 | 2048 | <2 |

Slab gel electrophoresis against myoglobin, chymotrypsinogen and human gamma globulin give the major fraction a M.W. of 20,500 to 21,500 and the minor protein a M.W. of about 28.000.

EXAMPLE XI

Carbohydrate Analysis-Phenol-sulfuric Acid Test

A standard curve was prepared by treating stock glucose solution with 0.1N aqueous sodium hydroxide and measuring the UV absorption at 485 nm. Runs on the Pittsburg 3-2 pili and the CDC B-2 pili indicates substantially the same amount of carbohydrate content, namely, 1.49±0.56% corresponding to 1-2 hexose residues per protein subunit.

EXAMPLE XII

Phosphorus Analysis (Method of Chen, et al, Anal. Chem. 28 1756 (1956))

The pili were digested in sulfuric acid and assayed against a potassium dihydrogen phosphate solution in water by the ammonium molybdate-ascorbic acid assay. The mean value for the Pittsburgh 3-2 pilus strains was 0.332±0.026% and for the CDC B-2 strain pili, 0.366±0.048%, indicating 2.5 and 2.3 phosphorus atoms per protein subunit respectively.

EXAMPLE XIII

Amino Acid Analysis of Type $T_2$ Pilus Crystals (Modified method of Spackman et al, Anal. Chem. 30, 1190 (1958)).

The analysis was run on a Beckman Spinco Model 120B Amino Acid Analyzer utilizing as internal standard norluceine and 2-amino-3-guanidino propionic acid. The protein sample (10 mg.) was hydrolyzed with concentrated hydrochloric acid at elevated temperatures (6N, 110° C.), for 24 hours in evacuated vials (0.025 mm.Hg.) Tryptophan analysis was estimated by the spectral method of Bence et al (Anal. Chem. 29, 1193, (1957)).

| aspartic + asparagine | 26 | isoleucine | 9 |
|---|---|---|---|
| alanine | 23 | arginine | 8 |
| glutamic + glutamine | 21 | tyrosine | 7 |
| lysine | 20 | proline | 6 |
| glycine | 17 | tryptophan | 4–5 |

-continued

| valine | 17 | histidine | 3 |
|---|---|---|---|
| serine | 14 | ½ cystine | 2 |
| leucine | 12 | methionine | 2 |
| threonine | 9 | phenylalanine | 2 |

Number of amino acids —200±9, m.w. 21,500±1000 daltons.

EXAMPLE XIV

Physical Properties

Solubility

Pilus crystals, appearing in an electron microscope as bundles of pilus rods, exist in the crystalline state about pH 5.5 and about pH 9.3. The crystals from $T_2$ variants start to separate into single pilus rods between pH 9.3 and pH 10.1. Above pH 10.1 they exist as single pilus rods. Similarly, the crystals of $T_1$ pili start to separate into single pilus rods at pH 7.7 and exist as rods above pH 8.6—i.e. the crystals are entirely disaggregated. Above about pH 11.0 $T_2$ pilus rods disassemble into smaller oligomeric units with a sedimentation constant of about 5.5.

The pilus crystals are soluble at pH 8.5 in 4M. aqueous sodium chloride, 50% aqueous sucrose and 20% saturated aqueous calcium chloride (both by weight). The crystals are also soluble in urea at 3M and above. However, treatment with urea at 3.5M or greater for more than 2 days leads to denaturation of the GC pili.

Ultracentrifugation

A GC pilus preparation (1 mg./ml.) was prepared in ethanolamine buffer (0.147 ionic strength, pH 10.1). The solution was run at 20 Krpm in a Beckman Spinco Model E Ultracentrifuge using an AN-D Rotor. Uncorrected sedimentatin rate S equals 37 svedbergs.

Pilus Rod Dimensions

GC pilus crystals were taken up in ethanolamine buffer at pH 10.0 with stacked disc rods of TMV protein negatively stained and examined in an electron microscope. The average diameter of GC pili is 83.4±2.3 Å.

EXAMPLE XV

PAT Test

Pilus crystals are suspended in TBS at pH 7.0 at a concentration of between 30 to 60 ug/ml. Non cloudy test serum is utilized. Where the test serum is cloudy it is centrifuged at 30 KG for 30 minutes and the supernate utilized. Serial dilutions of the serum are prepared and 0.025 ml. of the serum samples and 0.025 ml. of pilus crystal suspension are each charged to each Microtiter (trademark of Dynatech Laboratories) plate well and the mixture agitated for 30 minutes at ambient temperature. The wells are then read for crystal clumping in a dark field microscope.

The wells are then scored on the basis of maximum dilution which gives crystal agglutination observably greater than control.

Sample Test

White, New Zealand, female rabbits weighing from 4 to 6 pounds were injected subcutaneously with purified pilus preparations from CDCM-2, Pittsburgh 3-2, CDCT-2, CDC005-2 and Pittsburgh 4-2 strains, mixed 1:1 with Freund's Incomplete adjuvant and emulsified by syringing the mixture. About 100 to 200 μg/Kg. of pili was given in 3 injections about 2 weeks apart and the rabbits were bled 1 to 2 weeks after the 3rd injection. The blood was allowed to clot and the serum removed in the usual manner. The first 3 test sera were then run against pili from 21 *N. gonorrhoeae* strains and the results set forth in the Table below.

TABLE 1

PILUS CRYSTAL AGGLUTINATION TITRES OF PILI FROM 21 DIFFERENT STRAINS AGAINST SERA MADE WITH PILI FROM 3 DIFFERENT STRAINS

| Pilus Serum Strain | Pilus Strain | | | | | | | | | | | | | | |
|---|---|---|---|---|---|---|---|---|---|---|---|---|---|---|---|
| | Pittsburgh 3-2 | Pittsburgh 1-2 | Pittsburgh 4-2 | Pittsburgh 6-2 | CDC B-2 | CDC C-2 | CDC M-2 | CDC T-2 | Atlanta 4-2 | Atlanta 6-2 | Atlanta 9-2 | Seattle 1-2 | Seattle 3-2 | Atlanta 10-2 | CDC (Kellog) F62 |
| CDCM-2 | 16 | 256 | 16 | 64 | 8 | 32 | 12* | 8 | 16 | <8 | 8 | 16 | 32 | 32 | 8 |
| Pittsburgh 3-2 | 256 | 16 | 8 | 64 | 312 | <8 | 8 | <8 | 16 | 64 | 8 | 16 | 16 | 32 | 8 |
| CDC-T-2 | 4 | 16 | <4 | <4 | 3 | 32 | 16 | 312 | 32 | 8 | 32 | 64 | 14 | 8 | 128 |

| | Pittsburgh 7-2 | Norfolk 2-2 | Norfolk 7-2 | Dayton 8-2 | Seattle 9-2 | CDC *005-2 |
|---|---|---|---|---|---|---|
| CDC M-2 | 16 | 64 | 8 | 16 | 16 | 32 to 64 |
| Pittsburgh 3-2 | 128 | 64 | 13 | 64 | 128 | 128 |
| CDC T-2 | 16 | 32 | 8 | 8 | 16 | 64 |

*005 is a CDC strain isolated from a patient with disseminated CC infection.

EXAMPLE XVI

Serotyping

The PAT tests of Example XV indicated 3 or 4 strains had pili carrying only one determinant. This was confirmed by running sera derived from pili of four selected strains against the corresponding pili. The results are set forth in the Table below. The maximum response has been normalized to 100 to adjust for the different titres.

| Antisera Pili | Pittsburgh 3-2 | CDC M-2 | CDC T-2 | Pittsburgh 4-2 | Antigenic Determinant |
|---|---|---|---|---|---|
| Pittsurgh 3-2 | 100 | 3 | 2 | 1 | a |
| CDC M-2 | 3 | 100 | 1 | 2 | b |
| CDC T-2 | 0.4 | 2 | 100 | 2 | c |
| Pittsburgh 4-2 | 2 | 2 | 1 | 100 | d |

Serotyping of Strains of Unknown Determinant Composition

Pili are grown from the strains under test and run against antisera against the pili carrying the single determinants a, b, c and d. In the PAT Test the pili showed agglutination with one or more single determinants as shown in the Table below.

| Strain | | Serotype | | | |
|---|---|---|---|---|---|
| Pittsburgh | 3-2 | a | — | — | — |
| CDC | M-2 | — | b | — | — |
| CDC | T-2 | — | — | c | — |
| Pittsburgh | 4-2 | — | — | — | d |
| Norfolk | 7-2 | — | — | — | d |
| CDC | 8-2 | — | b | — | — |
| Pittsburgh | 6-2 | — | b | — | — |
| CDC | 0-2 | a | — | c | — |
| CDC | 005-2 | a | b | c | d |
| Norfolk | 2-2 | — | b | — | d |
| Seattle | 1-2 | — | — | c | — |
| Seattle | 3-2 | a | — | — | — |
| Dayton | 8-2 | — | b | a | d |
| Atlanta | 4-2 | — | b | — | — |
| Atlanta | 6-2 | — | b | — | — |
| Atlanta | 10-2 | a | b | — | — |
| Atlanta | 9-2 | — | b | — | d |

EXAMPLE XVII

Hemagglutination by GC Pili Preparations

General Methods

Type O human blood containing EDTA as anticoagulant was obtained from a blood bank. Red Blood cells were freshly prepared by washing an aliquot of blood 4 times with 15 volumes of pH 7.3, 0.01M phosphate-buffered saline, and making a 3% (by volume) suspension in the same buffer.

Solutions of 1.0 mg/ml Pittsburgh 3-2 and CDCM-2 pili were made up using the ultraviolet absorbance of the preparations at 280 nm, corrected for scattering, as a measure of concentration. Aliquots (50λ) of the 1.0 mg/ml solutions of pili are placed in the first well of a U-bottom Cooke Microtitre plate, 25λ of Tris-buffered saline+0.02% azide in all other wells, and the pili diluted with a 25λ hand operated micro diluter out through the 12th well.

Tris buffered saline or saline (25λ) and 25λ 3% red blood cell suspension is added to each test well, the plate agitated gently to mix, and placed at 4° C. Results are read after 1-2 hours with the aid of a light box.

| Results | |
|---|---|
| The degrees of hemagglutination observed are: | |
| 5+ | No cell pellet or clumps; even red color in well |
| 4+ | Trace of cell pellet |
| 3+ | Small cell pellet with very distinct fringe of cell clumps |
| 2+ | Distinct cell pellet with a fringe of moderate number of clumps |
| + | Distinct cell pellet with a few clumps up the sides of the well. |

Titres for both CDCM-2 and Pittsburgh 3-2 pili were done on two different occasions and are shown in the Table below and constitute control tests.

| Well | Serum Dilution | Pre-Adsorption | Post-Adsorption |
|---|---|---|---|
| 5 | 1/32 | 2+ | 0 |
| 6 | 1/64 | + | 0 |
| 7 | 1/128 | | 0 |
| 8 | 1/256 | | 0 |
| 9 | 1/512 | | 0 |
| 10 | 1/1024 | | 0 |
| 11 | 1/2048 | | 0 |
| 12 | 1/4096 | | 0 |

Removal of Ab-Ag Complexes

Serial dilutions of RBC-adsorbed rabbit preimmune and anti-CDCM-2 sera prepared as above were made in saline. Aliquots (0.1 ml) of each dilution were added to 0.1 ml of 100γ/ml M-2 pili in 1.5 ml Microfuge tubes. The tubes were incubated upright on a Yankee Rotator for 1 hour at 37° C. They were then spun 1 minute in the Beckman Microfuge. Slightly over half of the supernatant was removed and 50λ of each antiserum dilution placed in each of 2 wells of a Microtitre plate. A 25λ aliquot of 3% RBCs in phosphate buffered saline was

HEMAGGLUTINATION RESULTS

| | FIRST RUN | | | SECOND RUN | | | |
|---|---|---|---|---|---|---|---|
| Well # | Final Conc. Pili In Well 3-2 and M-2 | Degree of Agglutination 3-2 Pili | Degree of Agglutination M-2 Pili | Final Conc. Pili In Well 3-2 | Degree of Agglutination 3-2 Pili | Final Conc. M-2 In Well | Degree of Agglutination M-2 Pili |
| 1 | 333 Y/ml | 3+ | 3+ | 430 Y/ml | 3+ | 92 Y/ml | 3+ |
| 2 | 166.6 Y/ml | 4+ | 4+ | 225 Y/ml | 3+ | 46 Y/ml | 3+ |
| 3 | 83.3 Y/ml | 3+ | 4+ | 112.5 Y/ml | 3+ | 23 Y/ml | 3+ |
| 4 | 41.6 Y/ml | 3+ | 4+ | 36 Y/ml | 4+ | 11.5 Y/ml | 4+ |
| 5 | 20.8 Y/ml | ± | 3+ | 28 Y/ml | + | 5.0 Y/ml | + |
| 6 | 10.4 Y/ml | 0 | 3+ | 16 Y/ml | 0 | 2.0 Y/ml | ± |
| 7 | 5.2 Y/ml | 0 | 2+ | 70 Y/ml | 0 | 1.4 Y/ml | 0 |
| 8 | 2.6 Y/ml | 0 | ± | 3.3 Y/ml | 0 | 0.7 Y/ml | 0 |
| 9 | 1.3 Y/ml | 0 | 0 | 1.75 Y/ml | 0 | 0.35 Y/ml | 0 |
| 10 | 0.6 Y/ml | 0 | 0 | 0.88 Y/ml | 0 | 0.17 Y/ml | 0 |
| 11 | 0.3 Y/ml | 0 | 0 | 0.44 Y/ml | 0 | 0 | |
| 12 | 0.15 Y/ml | 0 | 0 | 0.22 Y/ml | 0 | 0 | |

Inhibition of Hemagglutination Removal of Ab-Ag Complex from Antiserum-Pili Mixtures before Titering for Hemagglutination Methods To eliminate background hemagglutination by sera alone 0.1 ml of undiluted washed red blood cells (RBCs) were added to 1 ml portions of antisera in glass round-bottom centrifuge tubes. The tubes were capped tightly with para-film and placed upright in a rack on a Yankee Rotator at 4° C. After 1 hour-10 minutes, the sera were spun at 2400 rpm in a refrigerated International Centrifuge, and tested for hemagglutination ability. The sera were further clarified by centrifugation at 12,000 G in a Sorvall RC-2 centrifuge.

Absorption of background hemagglutination factors at various dilutions pre and post RBC treatment of the antiserum is summarized in the following Table.

| Well | Serum Dilution | Pre-Adsorption | Post-Adsorption |
|---|---|---|---|
| 1 | ½ | 4+ | 2+ |
| 2 | ¼ | 3+ | + |
| 3 | ⅛ | 3+ | + |
| 4 | 1/16 | 3+ | 0 | added, the plate gently agitated to mix and left at 4° for 1 hour.

The results are set forth in the Table below. Where in place of CDC-M-2 pili other pili are utilized, similar results are obtained with sera containing antibodies against said pili.

| Conc. of Serum Against CDCN-2 Pili During Incubation With 50 Y/ml M-2 Pili | Hemagglutination Titres In Duplicate Rows | |
|---|---|---|
| | C | E |
| 1/10 | + | + |
| 1/20 | 0 | 0 |
| 1/40 | 0 | 0 |
| 1/80 | ± | ± |
| 1/160 | + | + |
| 1/320 | 2+ | 2+ |
| 1/640 | 3+ | 3+ |
| 1/1280 | 2+ | 2+ |
| 1/2560 | 2+ | 2+ |
| 1/10 Pre-immune Rabbit | 2+/3+ | 2+/3+ |

*Note that the Anti CDCM-2 Serum Alone has a + Hemagglutination at ⅛ Dilution

EXAMPLE XVIII

Human Test $T_2$ Pilus crystal from Pittsburgh 3-2 organisms were prepared, preserved with 0.01% merthiolate and emulsified with Freund's incomplete adjuvant. Human male volunteer test subjects were injected with the pilus suspension. Subject B received three injections of 2.2 μg/kg, 2.2 μg/Kg and 55 μg/Kg at intervals of 2 weeks. Subject R received three injections of 11 μg/Kg, 11 μg/Kg and 55 μg/Kg at the same intervals. The PAT titres of both subjects rose to 100 after the first injection and to over 200 over the next 4 months.

The subjects were challenged by the intraurethral introduction of a predetermined number of organisms of the same strain, the virulence of which had been previously tested. The same organism was administered to three unimmunized control subjects—T, S and M.

The test results are set forth in the Table below:

Resisting and Infecting Doses of Pittsburgh 3-2 Gonococci for Pilus-Immunized and Non-immunized Human Subjects

| Infectious Dose | Subjects Infected | Subjects Resisting |
| --- | --- | --- |
| 4 Orginal Subjects | | |
| $8 \times 10^1$ | T | B*, R*, S |
| $3 \times 10^2$ | | B*, R*, S |
| $8 \times 10^3$ | S | B*, R* |
| $3 \times 10^4$ | B*, R* | |
| 1 additional subject | | |
| $8 \times 10^1$ | | M |
| $3 \times 10^2$ | | M |
| $8 \times 10^2$ | | M |
| $1 \times 10^3$ | M | |

*Immunized

In accordance with the above procedures, in place of merely using pili with a single determinant a composite dose of pili carrying all determinants may be used.

Analysis of Results

Probability analysis of the foregoing results shows that the $ID_{50}$ of a nonimmune subject is $50 \times 10^2$ organisms and $2.0 \times 10^4$ for immune subjects.

Other experimental work has shown the probability of a male being infected by an infected female is about 30% caused by about 250 organisms being introduced into the male urethral tract during intercourse.

The results of the tests of the present invention indicate that the probability of infection of a male by an infected female during intercourse falls from 30% to 0.86% as a result of immunization to a PAT titer of 100 to 200.

We claim:

1. Material selected from the group consisting of single rod and agglomerated rod material derived from N. gonorrhoeae pili which is substantially free of cells or cell debris and which, when agglomerated, shows strong agglutination ability against sera containing antibodies against pili derived from at least one of the strains of N. gonorrhoeae designated Pittsburgh 3-2 (ATCC 31149), CDCT-2 (ATCC 31150), CDCM-2 (ATCC 31148) and Pittsburgh 4-2 (ATCC 31151), and is insoluble below pH 7.7 and soluble above pH 9.2.

2. A material of claim 1 showing strong agglutination activity against sera containing antibodies against pili derived from at least one of the following strains of N. gonorrhaeae those designated Pittsburgh 3-2 (ATCC 31149), CDCT-2 (ATCC 31150), CDCM-2 (ATCC 31148), Pittsburgh 4-2 (ATCC 31151) and which has the appearance of single rods in an electronmicroscope and a sedimentation rate of about 37 S at pH 10.1 in ethanolamine buffer, the said rods having a diameter of about $83.4 \pm 2.3$ Å.

3. A vaccine composition comprising the material of claim 1 and a pharmaceutically acceptable medium said composition being suitable for subcutaneous or intramuscular injection.

4. A method of protecting subjects in need of same against infection by a piliated strain of N. Gonorrhoeae, the pili of which exhibit immuno agglutination activity with sera containing antibodies against pili derived from at least one of the strains of N. Gonorrhoeae designated Pittsburgh 3-2 (ATCC 31149), CDCT-2 (ATCC 31150), CDC M-2 (ATCC 31148) and Pittsburgh 4-2 (ATCC 31151) which comprises administering to said subjects an effective amount of a composition of claim 1.

5. A material selected from the group consisting of single rods and agglomerated rods of the material of claim 1 isolatable from pili of type $T_1$ cultures of N. Gonorrhoeae, which is substantially free of cells or cell debris and when agglomerated showing strong agglutination against sera containing antibodies against pili derived from at least one of the following strains of N-Gonorrhoeae; those designated Pittsburgh 3-2 (ATCC 31149), CDCT-2 (ATCC 31150), CDCM-2 (ATCC 31148), Pittsburgh 4-2(ATCC 31151).

6. A agglomerated rod material of claim 5, isolatable from pili of Type $T_1$ cultures of N. gonorrhoeae, said agglomerated rod material being soluble in aqueous buffer above pH 8.6 and insoluble below pH 7.7, and showing strong agglutination against sera containing antibodies against pili derived from at least one of the following strains of N. gonorrhoeae those designated Pittsburgh 3-2 (ATCC 31149), CDCT-2 (ATCC 31150), CDCM-2 (ATCC 31148), Pittsburgh 4-2 (ATCC 31151).

7. $T_1$ Gonococcal pilin, being a phosphoglycoprotein isolatable from the rods of claim 5 of Type $T_1$ N. gonorrhoeae, said phosphoglycoprotein being a peptide chain of $200 \pm 9$ amino acids having between 2 and 3 phosphate groups and between 1 and 2 hexose sugars covalently bound to said chain, said chain having a molecular weight of $22,000 \pm 1000$, being substantially soluble in aqueous media at pH values greater than 8.5 and substantially insoluble in aqueous media at pH values less than 7.7, at 20° C.

8. A material selected from the group consisting of single rods and agglomerated rods of the material of claim 1 isolatable from pili of type $T_2$ cultures of N. Gonorrhoeae, which is substantially free of cells or cell debris and when agglomerated showing strong agglutination against sera containing antibodies against pili derived from at least one of the following strains of N-Gonorrhoeae; those designated Pittsburgh 3-2 (ATCC 31149), CDCT-2 (ATCC 31150), CDCM-2 (ATCC 31148), Pittsburgh 4-2 (ATCC 31151).

9. A agglomerated rod material of claim 8 isolatable from the pili of Type $T_2$ cultures of N. Gonorrhoeae, said agglomerated rod material being soluble in aqueous buffer above pH 9.2 and isoluble below pH 8.7, and showing strong agglutination against sera containing antibodies against pili derived from at least one of the following strains of N. Gonorrhoeae; those designated Pittsburgh 3-2 (ATCC 31149), CDCT-2 (ATCC 31150), CDCM-2 (ATCC 31148), Pittsburgh 4-2 (ATCC 31151).

10. $T_2$ Gonoccoccal pilin, being a phosphoglycoprotein isolatable from the rods of claim 8 of Type $T_2$ *N. gonorrhoeae*, said phosphoglycoprotein being a peptide chain of $200\pm9$ amino acids having between 2 and 3 phosphate groups and between 1 and 2 hexose sugars covalently bound to said chain, said chain having a molecular weight of $21,500\pm1000$ daltons, being substantially soluble in aqueous media at pH values greater than 10.1 and substantially insoluble in aqueous media at pH values less than 8.6, at 20° C.

11. A method of isolating gonococcal pilin said pilin being defined in claim 7 or claim 10 which comprises subjecting pili of *N. gonorrhoeae* to polyacrylamide gel electrophoresis and removing from said gel the major fraction stainable by Coomassie Blue.

12. A composition consisting substantially of at least 92% of $T_1$ or $T_2$ gonococcal pilin as defined in claim 7 or claim 10 and between 6 and 8% of a protein derived from the pili of cultures of Type $T_1$ or $T_2$ *N. gonorrhoeae* and having a molecular weight of about 28,000 daltons, said composition being dissociable into single rods consisting of said protein and said gonococcal pilin at a pH above pH 9.3, the rods having a sedimentation rate of about 37 S at pH 10.1 in ethanolamine and having a diameter of $83.4\pm2.3$ Å.

13. A composition according to claim 12 wherein the single rods have a density at pH 10.1 of 1.35 to 1.33 g/ml.

14. A composition according to claim 12 and including $T_2$ gonococcal pilin wherein the ratio of amino acids in said composition is:

| aspartic + asparagine | 26 | isoleucine | 9 |
| alanine | 23 | arginine | 8 |
| glutamic + glutamine | 21 | tyrosine | 7 |
| lysine | 20 | proline | 6 |

| -continued | | | |
|---|---|---|---|
| glycine | 17 | tryptophan | 4-5 |
| valine | 17 | histidine | 3 |
| serine | 14 | ½ cystine | 2 |
| leucine | 12 | methionine | 2 |
| threonine | 9 | phenylalanine | 2 |

15. A composition according to claim 12, which is a agglomerated rod composition.

16. A composition according to claim 15 wherein the single rods have a density at pH 10.1 to 1.35 to 1.33 g/ml.

17. A method of testing for the presence of antibodies to *N. Gonorrhoeae* pili comprising the steps, carried out in vitro, of:
    (a) treating material selected from the group consisting of single rod and agglomerated rod material derived from *N. Gonorrhoeae* pili which is substantially free of cells or cell debris and which, when agglomerated, shows strong agglutination ability against sera containing antibodies against pili derived from at least one of the strains of *N. Gonorrhoeae* designated Pittsburgh 3-2 (ATCC 31149), CDCT-2 (ATCC 31150), CDCM-2 (ATCC 31148) and Pittsburgh 4-2 (ATCC 31151), and is insoluble below pH 7.7 and soluble above pH 9.2 with a sample of serum suspected of containing said antibodies thereto, and
    (b) observing the occurrence of agglutination of said crystals or said rods, the presence of said agglutination indicating the presence of the antibodies in the serum.

18. A method according to claim 17 wherein the agglutination is observed with a dark field microscope.

19. A method according to claim 17 or claim 18 including the steps of diluting the serum with predetermined amounts of an immunologically inactive diluent and determine the dilution at which no observable crossreactivity occurs in order to determine relative concentrations of antibodies of the serum.

* * * * *